(12) United States Patent
Morris

(10) Patent No.: US 9,041,939 B2
(45) Date of Patent: May 26, 2015

(54) APPARATUS AND METHOD FOR COMPENSATING FOR SAMPLE MISALIGNMENT

(75) Inventor: Stephen Morris, Shrewsbury (GB)

(73) Assignee: NIGHTINGALE-EOS LTD, Wrexham (GB)

( * ) Notice: Subject to any disclaimer, the term of this patent is extended or adjusted under 35 U.S.C. 154(b) by 171 days.

(21) Appl. No.: 13/699,888

(22) PCT Filed: May 26, 2011

(86) PCT No.: PCT/GB2011/000811
§ 371 (c)(1), (2), (4) Date: Nov. 26, 2012

(87) PCT Pub. No.: WO2011/148143
PCT Pub. Date: Dec. 1, 2011

(65) Prior Publication Data
US 2013/0070245 A1    Mar. 21, 2013

(30) Foreign Application Priority Data
May 28, 2010 (GB) .................... 1009039.7

(51) Int. Cl.
*G01B 11/24* (2006.01)
*G01N 21/21* (2006.01)

(52) U.S. Cl.
CPC ..................... *G01N 21/21* (2013.01)

(58) Field of Classification Search
CPC .... G02B 6/262; G02B 6/4206; G02B 6/4214; G02B 6/4225; G02B 6/4246; G02B 21/0016; G02B 21/006; G02B 21/0064; G02B 26/06; G02B 6/02052; G02B 6/06; G02B 6/29368; G02B 6/3624; G02B 6/42
See application file for complete search history.

(56) References Cited

U.S. PATENT DOCUMENTS

| | | | |
|---|---|---|---|
| 4,999,014 A | 3/1991 | Gold et al. | |
| 5,042,951 A | 8/1991 | Gold et al. | |
| 5,136,149 A | 8/1992 | Fujiwara et al. | |

(Continued)

FOREIGN PATENT DOCUMENTS

| | | |
|---|---|---|
| DE | 102004016322 A1 | 10/2004 |
| JP | S62267606 A | 11/1987 |

(Continued)

OTHER PUBLICATIONS

Groenewald B. et al. "Substrate Curvature Measurement System," Dielectric Materials, Measurements and Applications Conference, pp. 458-463 (IEE 2000).

(Continued)

*Primary Examiner* — Michael P Stafira
(74) *Attorney, Agent, or Firm* — Morgan, Lewis & Bockius LLP

(57) ABSTRACT

A method of compensating for sample misalignment in an optical measurement apparatus (40), comprises the steps of: determining an expected response from a detector (58) in said optical measurement apparatus given a particular set of parameters defining a path that light can take through the optical measurement apparatus from a source (42), via a sample (50), to the detector (58); measuring a response from the detector for the sample under test; and refining the set of parameters until the expected response and the measured response converge so as to determine the set of parameters giving rise to the measured response.

19 Claims, 5 Drawing Sheets

(56) References Cited

U.S. PATENT DOCUMENTS

| | | | |
|---|---|---|---|
| 6,677,565 | B1 | 1/2004 | Wahl et al. |
| 6,744,510 | B2 | 6/2004 | Gweon et al. |
| 7,081,957 | B2 | 7/2006 | Norton |
| 7,230,705 | B1 * | 6/2007 | Yang et al. ............... 356/401 |
| 7,236,680 | B1 * | 6/2007 | Jordan ..................... 385/147 |
| 7,327,452 | B2 | 2/2008 | Frank et al. |
| 7,583,388 | B2 | 9/2009 | Seko et al. |
| 7,978,932 | B2 * | 7/2011 | Vercauteren et al. ....... 382/284 |
| 8,760,756 | B2 * | 6/2014 | Price et al. ............... 359/368 |
| 2004/0100894 | A1 | 5/2004 | Ninomiya et al. |
| 2005/0083537 | A1 * | 4/2005 | Kuchel .................... 356/513 |
| 2006/0039643 | A1 * | 2/2006 | Saaski ..................... 385/12 |
| 2007/0077009 | A1 * | 4/2007 | Luyssaert et al. .......... 385/49 |

FOREIGN PATENT DOCUMENTS

| | | |
|---|---|---|
| JP | S6358119 A | 3/1988 |
| JP | 3326931 B2 | 9/2002 |
| JP | 2006260487 A | 9/2006 |
| WO | WO-2008119982 A1 | 10/2008 |
| WO | WO-2008119984 A1 | 10/2008 |

OTHER PUBLICATIONS

Fan Hua et al. "Novel Optical Sensor for precise Tilt Angle Measurement", Control, Automation, Robotics and Vision, 2006. ICARCV '06. 9th International Conference ON, IEEE, PI, Dec. 5, 2006, pp. 104.

International Search Report issued for International Application No. PCT/GB2011/000806 on Oct. 4, 2011 and mailed on Oct. 12, 2011.

International Search Report issued for International Application No. PCT/GB2011/000811 on Nov. 4, 2011 and mailed on Nov. 15, 2011.

* cited by examiner

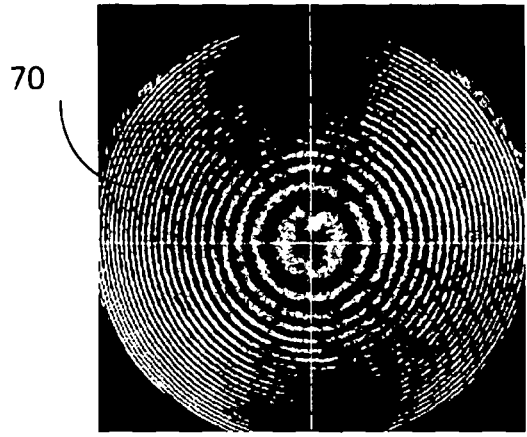
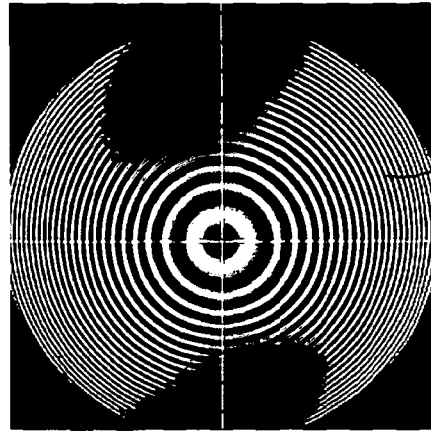
Fig 3A         Fig 3B
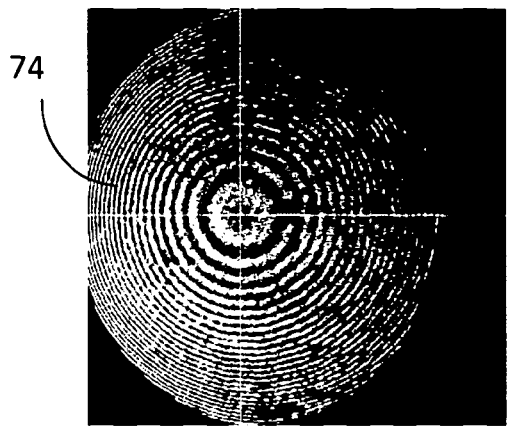
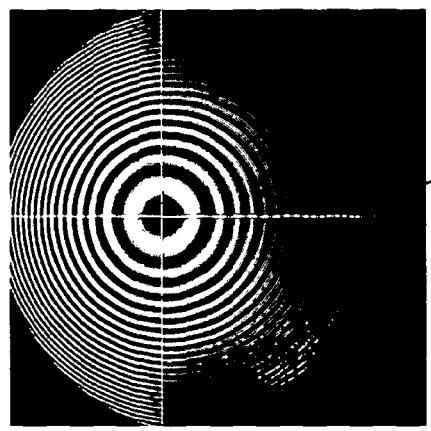
Fig 4A         Fig 4B

APPARATUS AND METHOD FOR COMPENSATING FOR SAMPLE MISALIGNMENT

CROSS-REFERENCE TO RELATED APPLICATIONS

This application is a U.S. National Phase Application of PCT/GB2011/000811, filed May 26, 2011, which claims priority to and the benefit of United Kingdom Patent Application No. 1009039.7, filed May 28, 2010. The entire disclosure of each of these applications is incorporated by reference herein.

FIELD OF THE INVENTION

This invention relates to an apparatus and method for compensating for sample misalignment.

BACKGROUND TO THE INVENTION

Beam Profile Reflectometry (BPR) and Beam Profile Ellipsometry (BPE), described in U.S. Pat. Nos. 4,999,014 and 5,042,951 respectively, are established methods for measuring the thicknesses of thin films and coatings deposited upon flat substrates. Each of these techniques makes use of data contained in the cross-sectional profile of a laser beam which has been reflected from the sample under test. As described in each of these patents, each technique relies on the sample under test being (a) perfectly flat and (b) aligned so that an incident probe beam is focused substantially normal to the surface of the sample.

In practice, known implementations of BPR rely on a very high degree of accuracy in achieving this alignment, since only when the alignment is perfect are the beam profiles obtained symmetrical, and this in turn is an assumption made in the subsequent analysis. To this end, the present inventor has devised a sophisticated five-axis stage arrangement (described in WO2008/119982) which, when used in combination with optical feedback from a BPR system, can be used to align a sample (including samples with complex shapes) to an arbitrarily high degree of accuracy.

However, the requirement for this alignment (whether achieved statically for flat samples by very accurate construction of supporting hardware, or dynamically for curved surfaces using a stage such as that referred to above) introduces significant cost and complexity into a BPR or BPE system.

It is therefore an aim of the present invention to provide an apparatus and method that addresses at least some of the afore-mentioned problems.

SUMMARY OF THE INVENTION

According to a first aspect of the present invention there is provided a method of compensating for sample misalignment in an optical measurement apparatus, comprising the steps of:
  determining an expected response from a detector in said optical measurement apparatus given a particular set of parameters defining a path that light can take through the optical measurement apparatus from a source, via a sample, to the detector;
  measuring a response from the detector for the sample under test; and
  refining the set of parameters until the expected response and the measured response converge so as to determine the set of parameters giving rise to the measured response.

The set of parameters may comprise parameters defining the material and/or physical properties of the sample. More specifically, the set of parameters may comprise parameters defining the nature of the sample surface and/or its orientation/alignment relative to the optical measurement apparatus. The nature of the sample surface may be determined by one or more of its shape, its structure or its composition including, for example, the thickness of one or more coatings on the sample and/or the curvature of one or more coatings on the sample.

Embodiments of the invention effectively provide a method which can be used to correct for sample misalignment during optical measurements. The proposed method provides a different approach for analyzing measured responses, such as those obtained during a Beam Profile Reflectometry (BPR) measurement. Traditionally, in such measurements a correction will be applied to the measured data (response), for example, to obtain the reflectance of the sample, before regression analysis is applied to the corrected data to obtain, say, the coating properties of the sample. In the present case, however, the comparison is performed directly between an uncorrected measurement and a known (i.e. expected) result. It is therefore not necessary to correct the measured data for misalignment and nor is it necessary to correctly align the sample prior to the measurements being taken. Accordingly, the cost of constructing an apparatus for performing optical measurements can be substantially reduced and the process of collecting data for analysis can also be greatly accelerated. As a result, the present aspect of the invention allows one or more properties of the sample to be determined in a less expensive and less time-consuming manner than previously.

Particular embodiments of the present invention may be able to compensate for substantial misalignments, for example up to a significant proportion of a main objective lens' numerical aperture. Furthermore, effects such as the misalignment of a light source relative to a main objective lens can also be ameliorated by the present invention.

It is noted that, with the present invention, no assumptions are required to be made about the alignment of the sample when making a measurement. Instead, the parameters describing the sample's alignment may simply be treated as 'floating variables' in the same way as parameters describing a sample's coating characteristics, for example. Accordingly, sample misalignment (as well as coating characteristics such as thickness and composition) can form parameters that can be measured.

The method of the present invention may be configured to provide simultaneous coating-and-orientation characterisation of a sample. This may be performed by an optical measurement apparatus configured for Beam Profile Reflectometry (BPR) and/or Beam Profile Ellipsometry (BPE). Applications of this method could include measuring film thicknesses on silicon wafers that have naturally warped or bowed (e.g. as a result of stress in the coatings applied to them), without first having to make the wafers flat by sucking them flat onto a vacuum stage. The fact that the amount of warp or bow can be measured simultaneously with the film thickness eliminates the need for a separate measurement to be taken and also reduces the amount of wafer handling required. Other applications of the present invention include measuring coating thicknesses on relatively small engineered parts, particularly those that have complex structures such as MEMS or medical devices.

In embodiments of the present invention, the step of determining the expected response may comprise the calculation of a reflected intensity (rather than the calculation of a reflectance). In alternative embodiments, the step of determining the expected response may comprise the calculation of a reflectance.

The step of determining the expected response from the detector may comprise ray-tracing analysis. The ray-tracing analysis may comprise determining the path of a light ray emerging from a light source and being reflected from the sample to the detector.

The light source may be constituted by a laser.

The ray-tracing analysis may further comprise determining the path of the light ray through one or more optical elements. The optical elements may be constituted by a lens (e.g. an objective lens or a relay lens), a beamsplitter, a retarder, a polarizer or an analyzer.

In a particular embodiment, the ray-tracing analysis may be performed from the detector to the light source. In other words, 'time-reversal' may be applied in the ray-tracing analysis.

Using 'time reversal' in the ray-tracing analysis is advantageous in that it can substantially reduce the size of the calculation that must be carried out and therefore it can be used to simplify and accelerate the procedure. The reason that this approach can substantially reduce the size of the calculation will become apparent from consideration of the following. It will be understood that the parameters describing the misalignment of the sample are continuous in nature (i.e. the surface of the misaligned sample is continuous so light can reflect from it at any location) but the light-sensitive elements of a physical detector are discrete (i.e. the detector is composed of a plurality of individual detector elements or pixels). If a ray is considered to start from a certain location (x, y) within a source beam and is followed through an optical system to a detector at a location (x', y'), it may reach the detector at a position close to an individual detector element's centre, at its edge or even between elements. In order to calculate correctly the final intensity value recorded by the detector element at (or closest to) (x', y'), it is necessary to know not only the amplitude and phase of the light ray that originated at (x, y) but also the amplitude and phase of all the other rays from the source beam that eventually arrive at the same detector element. When the rays themselves are of course not discrete but form part of a continuous light beam, this becomes a complicated calculation, involving a time-consuming interpolation step similar to that described in one of the applicant's earlier patent applications, published as WO2008/119984. It is therefore possible to reduce the size of the calculation by starting the ray-tracing analysis from the detector (in particular, from an individual detector element) since only those rays that will influence the detector response need be considered.

The ray-tracing analysis may comprise ray-tracing a light path starting from the detector, at the location of a given detector element, and following the ray backwards through the optical measurement apparatus to a point in its source. The step of determining the expected response from the detector may further comprise obtaining the amplitude of light from the source at said point. The step may then comprise using the amplitude and the transmission and/or reflection characteristics of the light path to determine the intensity of the light when it reaches the detector element.

The steps of ray-tracing the light path, obtaining the amplitude of light from the source and determining the intensity of the light at the detector element may be repeated for one or more alternative light paths that the light may travel through the apparatus and/or sample to arrive at the given detector element. For example, in the case of a curved sample, light travelling along two different paths may arrive at the same point on the detector.

The amplitude of light from the light source may be determined from an analytical function or a lookup table and/or these may be calibrated according to intensities measured from a sample with known reflectance and/or orientation.

The method may further comprise the step of combining the intensities of each light ray at the detector element to obtain the total intensity expected.

The method may further comprise repeating the above for a plurality of given detector elements. The method may comprise repeating the above for every given detector element so as to calculate a complete detector response. Alternatively, the above steps may be repeated for a subset of given detector elements—for example, to calculate the response from an array of horizontally-spaced and/or vertically-spaced given detector elements.

The method may comprise the step of generating a reflectance map wherein the value obtained at each given detector element corresponds to the reflectance coefficient of the sample for light that arrives at each given detector element. The reflectance map may be obtained by performing the above described ray-tracing analysis for a sample of known orientation and setting the reflectance of the sample to 100% (rather than whatever value would be obtained from the sample coating), and then dividing the measured intensity pattern by the calculated 100% reflectance.

The step of refining the set of parameters may comprise regression analysis. In some embodiments non-linear regression analysis may be employed. More specifically, the step of refining the set of parameters may comprise the use of a Levenberg-Marquardt algorithm.

The detector elements may be constituted by pixels such as those provided in a CMOS or CCD array.

The method may further comprise a calibration step. The calibration step may comprise determining the intensity characteristics of the light source and/or the alignment of optical elements within the optical measurement apparatus.

The method may be configured for compensating for sample misalignment during Beam Profile Reflectometry (BPR), Beam Profile Ellipsometry (BPE), Spectrophotometry, Spectroscopic Ellipsometry or an alternative optical measurement technique.

According to a second aspect of the present invention there is provided an optical measurement apparatus for compensating for sample misalignment, comprising:
  a detector for measuring a response from a sample under test; and
  a processor for determining an expected response from the detector given a particular set of parameters defining a path that light can take through the optical measurement apparatus from a source, via a sample, to the detector and for refining the set of parameters until the expected response and the measured response converge so as to determine the set of parameters giving rise to the measured response.

According to a third aspect of the present invention there is provided a carrier medium carrying computer readable program code configured to cause a computer to carry out the method according to the first aspect of the invention.

According to a fourth aspect of the present invention there is provided a device comprising:
  a program memory containing computer readable instructions; and
  a processor configured to read and execute instructions stored in said program memory;

wherein said processor readable instructions comprise instructions configured to control said device to carry out the method according to the first aspect of the invention.

The optional features described above in relation to the first aspect of the invention, apply equally to the second, third and fourth aspects of the invention, as appropriate.

The method and apparatus of the present invention may be employed in various applications and in a wide range of industries. In particular, the method and apparatus may find application in coating thickness metrology, for example, in semiconductor or medical device manufacturing.

BRIEF DESCRIPTION OF THE DRAWINGS

Embodiments of the invention will now be described, as examples only, with reference to the accompanying drawings, in which:

FIG. 3A illustrates a measured fringe for the example of a reasonably well-aligned cardiac stent, in accordance with an embodiment of the present invention;

FIG. 3B illustrates a calculated fringe for the stent of FIG. 3A with no misalignment applied, in accordance with an embodiment of the present invention;

FIG. 4A illustrates a measured fringe for the stent used to produced FIG. 3A but where the stent is misaligned, in accordance with an embodiment of the present invention;

FIG. 4B illustrates a calculated fringe for the stent of FIG. 4A with a degree of misalignment included in the calculation, in accordance with an embodiment of the present invention;

DETAILED DESCRIPTION OF CERTAIN EMBODIMENTS

Figure 1:
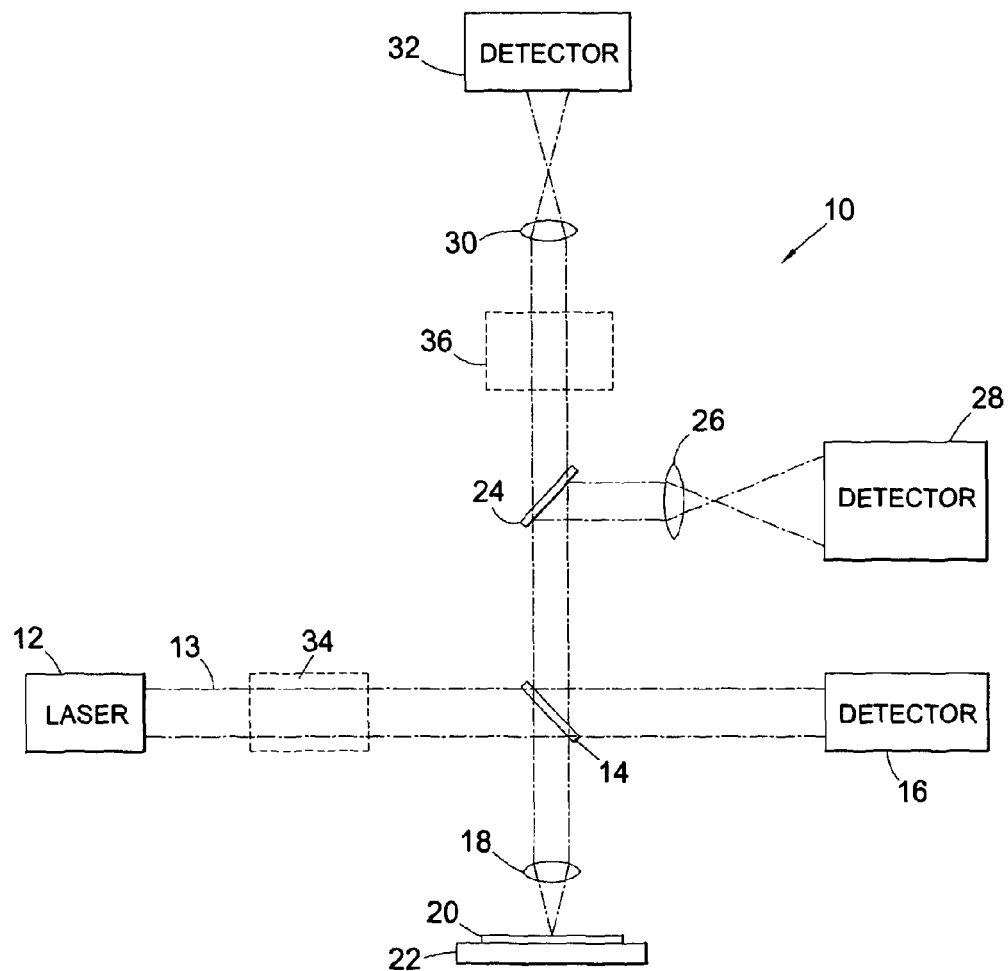
FIG. 1 illustrates schematically a typical known BPR system.

With reference to FIG. 1, there is illustrated a typical BPR system 10 in accordance with the prior art. The BPR system 10 comprises a laser source 12 from which a laser beam 13 emanates and is directed towards a first 45° angle beam splitter 14 (angled downwardly and forwardly with respect to the laser beam 13, as shown) and beyond which is positioned a first detector 16. A first objective lens 18 is provided in the path of light reflected downwardly from the first beam splitter 14, as illustrated. The first objective lens 18 is positioned to focus light from the laser source 12 onto the surface of a sample 20 aligned in a plane normal to the laser beam 13 on a stage 22. Light reflected from the sample 20 is passed back through the first objective lens 18 and the first beam splitter 14 until it encounters a second 45° angle beam splitter 24 (angled upwardly and forwardly with respect to the laser beam 13, as shown). Light reflected from the second beam splitter 24 is arranged to pass through a second lens 26 to image the laser beam 13 onto a second detector 28. Light passing through the second beam splitter 24 is arranged to pass through a third (relay) lens 30 to image the laser beam 13 onto a third detector 32. It will be noted that in this arrangement, the second detector 28 is configured to measure the full power of the reflected laser beam 13 and this information is used to enhance the sensitivity of the system 10. In other embodiments, the second beam splitter 24, second lens 26 and second detector 28 may be omitted.

A BPE system is substantially the same as the BPR system 10 illustrated in FIG. 1 except for the addition of appropriate polarisation-sensitive elements at suitable locations in the optical path. For example, one embodiment of such a BPE system could include a combination of a polarising element and a retarding element such as a quarter-wave plate at position 34 in FIG. 1, together with a second polarising element (referred to as an 'analyzer') at position 36 in FIG. 1. Another embodiment of a BPE system could include the retarding element being located just before the polarizer at position 36 instead.

The measurement directly made by the system 10 at the third detector 32 is the intensity of the laser beam 13 after it has been reflected from the sample 20. In order to obtain the reflectance of the sample 20, it is necessary to compare the beam intensity on reflection from the sample 20 with the beam intensity on reflection from a 'reference' with known reflectance—usually a piece of bare silicon. This procedure is very straightforward if it can be assumed that the alignments of the reference and the sample 20 under test are identical because then each pixel of data from the reference measurement corresponds to the same angle-of-incidence as the sample data from the same pixel. It is from this point that the data analyses described in U.S. Pat. Nos. 4,999,014 and 5,042,951 proceed. These analyses further assume that, with the sample 20 perfectly aligned, there exist perpendicular cross-sections through the reflected laser beam 13 corresponding to the cases of pure 's' polarisation and pure 'p' polarisation, respectively.

However, if the reference and the sample cannot be assumed to have identical alignments, then it is not possible to recover the sample reflectance at this stage. Moreover, even if it were, then for a misaligned sample there are no longer any beam cross-sections which contain pure 's' or pure 'p' polarisation—rather, along any given cross-section there will be mixture of 's' and 'p' polarisation, with the relative amounts of each varying along the length of the cross-section. Embodiments of the present invention therefore provide an alternative scheme of analysis which is based upon the direct calculation of reflected intensity, rather than reflectance. The only parameters that must be known in advance in this case are the intensity characteristics of the incident light beam and the alignment of individual optical elements within the system, all of which can be obtained during an initial calibration. Accordingly, when making a measurement from a sample, no assumptions need be made about its alignment. On the contrary, the parameters describing the sample's alignment are simply treated as 'floating variables' in the same way as the parameters that might describe the coating characteristics of the sample.

Figure 2:
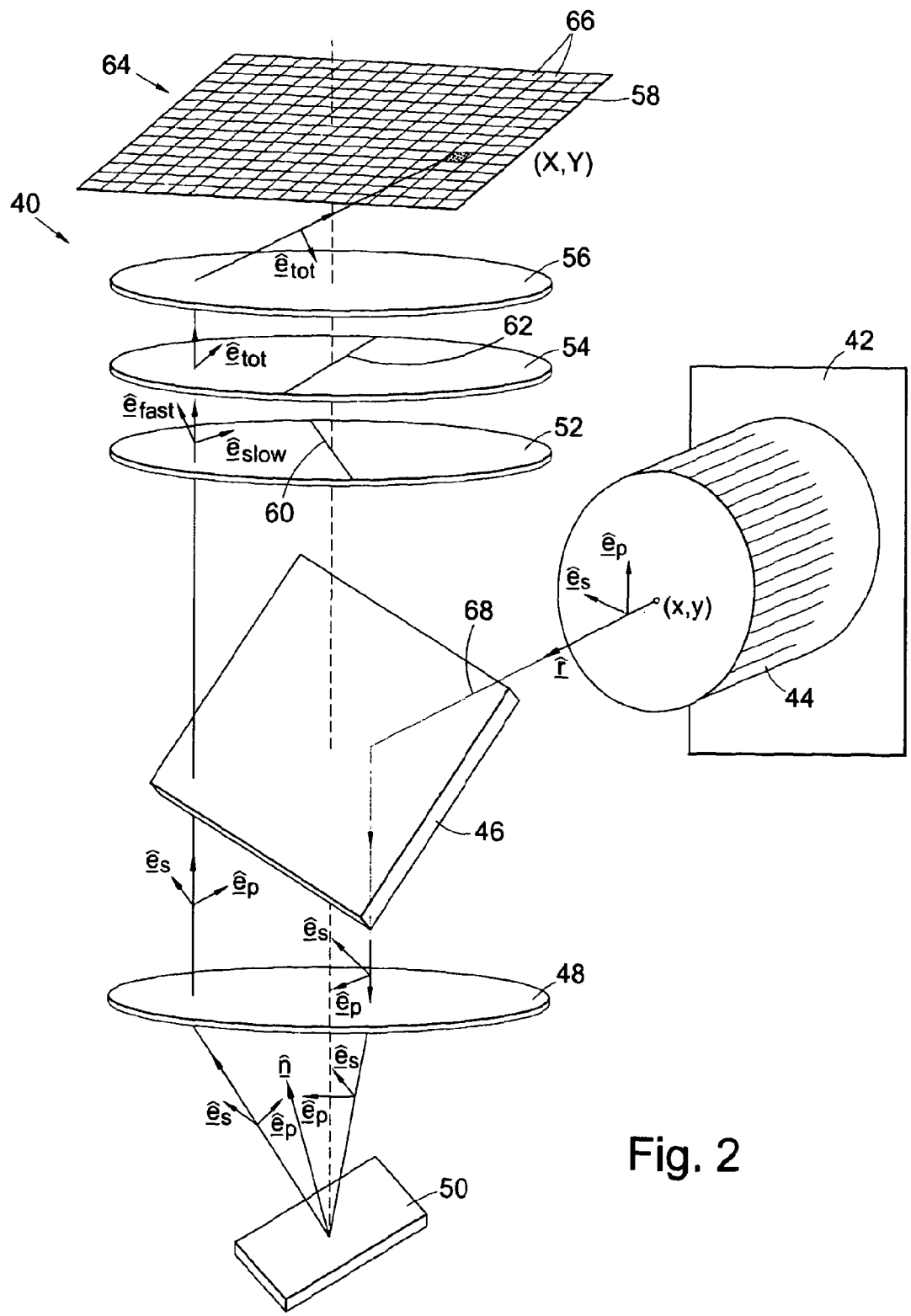
FIG. 2 illustrates a method and apparatus according to embodiments of the present invention, in a BPE system.

An embodiment of the present invention is illustrated in FIG. 2 for a particular BPE system 40. This system 40 comprises a laser source 42 generating an incident laser beam 44 which is directed towards a 45° angle beam splitter 46. In this embodiment, the beam 44 from the laser source 42 is assumed to be linearly polarised in either the horizontal or vertical direction, but in an alternative embodiment an additional linear polarising element can be provided in the beam between the source 42 and the beam splitter 46 in order to ensure that the beam has the preferred polarisation.

Light reflected from the beam splitter 46 passes through an objective lens 48 and is focused towards a sample 50. Light reflected from the sample 50 then passes through the beam splitter 46, through a retarder 52, through a polarizer 54 (also known as an analyzer) and through a relay lens 56 which forms an image of the reflected laser beam 44 on a detector 58.

The retarder 52 is constituted by a quarter-wave plate configured to introduce a quarter-wave phase shift between the orthogonal components of the incident laser beam 44. The retarder 52 has a fast axis 60 which in this embodiment is oriented parallel to the direction of polarisation of the incident beam 44 (although in other embodiments the fast axis 60 may be perpendicular to the direction of polarisation of the incident beam 44). The polarizer 54 is configured to allow just one linearly polarised component of the beam 44 to pass, while attenuating the component which is perpendicular to a polarisation axis 62 of the polarizer 54. In this embodiment, the polarisation axis 62 is oriented at an angle of 45 degrees relative to the fast axis 60 of the retarder 52.

The detector 58 comprises a photo-sensitive two-dimensional array 64. In the present embodiment, the array 64 is constituted by a CCD array comprising a plurality of individual pixels 66. In alternative embodiments, the detector may comprise a CMOS digital camera.

A further alternative embodiment is possible with the relative orientations of the 'source optics' and 'detector optics' reversed, that is to say, with the source 42 oriented so that the incident beam 44 passes straight through the beam splitter 46 towards the sample, whilst the reflected light is deviated by the beamsplitter towards the detector 58. In another embodiment, the source 42 and the detector 58 have the orientations shown but the objective lens 48 and sample 50 are located opposite the source 42, so that again the beam 44 from the source 42 passes straight through the beam splitter 46, while reflected light from the sample 50 is deviated by the beam splitter 46 towards the detector 58.

A method of compensating for sample misalignment according to an embodiment of the present invention will now be described in relation to the optical measurement apparatus 40 shown in FIG. 2. However, it will be understood that changes may be made to the apparatus 40 for alternative BPE configurations (for example, with the retarder 52 and polarizer 54 located elsewhere in the optical path) or for a BPR configuration (where they are simply omitted).

Firstly let us consider the progress of a particular ray of light 68 propagating through the system 40, where the ray 68 originates at a location (x, y) within the collimated incident laser beam 44. The ray 68 (along with every other ray making up the beam 44) is reflected from the beamsplitter 46 towards the main objective lens 48, is focused by the lens 48 to a point on the surface of the sample 50 (which is tilted by some unknown amount relative to the beam 44), is reflected by the sample 50 back towards the lens 48, is re-collimated by the lens 48, passes through the beamsplitter 46, then passes through the retarder 52, the polarizer 54 and finally the relay lens 56 which directs the ray 68 to the array 64 of the detector 58.

It will be noted that within each section of travel of the ray 68, we can calculate the directions of a number of unit vectors which are helpful to describe the characteristics of the light. In most cases, there are three such vectors: the vector representing the direction of the light itself ($\hat{r}$) and the vectors representing the directions of the 's' and 'p' components of the light's electric field vector, namely $\hat{e}_s$ and $\hat{e}_p$. These three vectors are always mutually perpendicular. As the light ray 68 passes through the retarder 52, it is more helpful to consider, in place of $\hat{e}_s$ and $\hat{e}_p$, the unit vectors parallel and perpendicular to the retarder's fast axis 60, which we denote $\hat{e}_{fast}$ and $\hat{e}_{slow}$, and after the light has passed through the polarizer 54 only the vector which is parallel to the axis of polarization 62, $\hat{e}_{tot}$, is relevant. A further unit vector, $\hat{n}$, represents the 'normal' to the tilted surface of the sample 50 at the focal point of the laser beam 44.

The method of compensating for sample misalignment according to this embodiment of the present invention involves the application of ray-tracing to determine an expected response from the detector 58 given a particular set of parameters defining the path that light rays can take through the optical measurement apparatus 40 from the source 42, via a sample 50, to the detector 58.

The progress of the ray 68, represented by the unit vector $\hat{r}$, from the point (x, y) in the laser beam 44 towards the focal point on the sample 50 depends only upon the alignment of the optical hardware (i.e. the beamsplitter 46 and objective lens 48) in this section of the apparatus 40 and this can be determined by a calibration step described in more detail below.

Given the direction of $\hat{r}$ as the ray 68 approaches the sample 50, plus the sample normal $\hat{n}$, it is possible to identify a 'plane of incidence' (i.e. a plane that includes both of these vectors) and thence the direction of $\hat{e}_p$ (which is perpendicular to $\hat{r}$ but within the plane of incidence) and $\hat{e}_s$ (which is perpendicular to both and $\hat{r}$ and $\hat{e}_p$). The directions of $\hat{r}$, $\hat{e}_s$ and $\hat{e}_p$ after reflection from the sample 50 depend only upon their pre-reflection values plus $\hat{n}$, their directions beyond the objective lens 48 depend on the known characteristics of the objective lens 48, and likewise the calculation of the $\hat{e}_{fast}$, $\hat{e}_{slow}$, $\hat{e}_{tot}$, and the ultimate point of arrival at the detector 58 are matters of straightforward vector geometry.

Note that at this point in the procedure, we are not yet considering the amplitude of the light ray 68 at any point along its path, merely the unit vectors which describe its path and its key electric field components. Even in this context, however, there is a serious problem which embodiments of the present invention aim to overcome, and which will now be described in detail. For a given combination of the starting point, (x, y), within the incident beam 44, and the misalignment of the sample 50 represented by $\hat{n}$, the final location at which the beam 44 arrives at the detector 58 may be any one of a continuum of possible locations because (x, y), and $\hat{n}$ are by their nature continuous variables. However, any practical detector 58 is a discrete device, with a finite number of pixels 66 at predetermined locations. If we were to begin a calculation at a regular grid of starting locations $(x_k, y_k)$ within the incident beam 44 and pursue the ray-tracing all the way through the system 40 to the detector 58, then it is likely that some rays 68 would arrive centrally within individual pixels 66, others near the edges or in the gaps between pixels 66, and some pixels 66 would be the destination for more than one ray 68 whilst other pixels 66 would appear to be in darkness. It is therefore not practical to do a realistic calculation of the intensity pattern at the detector 58 by proceeding on this basis.

The above problem is solved in the present embodiment by carrying out the ray-tracing in reverse, starting centrally within each discrete pixel 66 of the detector 58 and working backwards towards the source 42 of the beam 44. In this case, the path from any discrete detector pixel 66 $(X_k, Y_k)$ still maps onto a continuous location $(x'_k, y'_k)$ at the source 42 because of the continuous nature of $\hat{n}$, but as the intensity distribution of the laser beam 44 is itself a continuous function this does not matter. Carrying out the ray-tracing as described above, under a time-reversal principle, works because the equations that describe the geometrical transforms at each optical element (i.e. the polarizer 56, retarder 52, objective lens 48, sample 50 etc.), and the effects of each element upon the light intensity, are themselves time-invariant. A major advantage of this method is that it significantly simplifies the calculation since otherwise it would be necessary to use a grid of starting points at the source 42 with a density much higher than that of the pixels 66 at the detector 58, or to perform interpolation between the pattern of destination locations calculated at the detector 58 and the centres of the detector pixels 66—either of which would be extremely computationally intensive.

In the present embodiment, a further significant saving in computation time is realised by adopting the method described by Möller and Hughes in T. Möller and J. F. Hughes, "Efficiently Building a Matrix to Rotate One Vector to Another", Journal of Graphics Tools 4(4) 1-4 (1999), to calculate transformation matrices which describe the effect of the objective tens 48 upon the unit vectors $\hat{r}$, $\hat{e}_s$ and $\hat{e}_p$ describing the light ray 68, both as it is focused towards the sample 50 and as it is re-collimated upon leaving the sample 50. Given a pair of vectors $\hat{r}$ and $\hat{r}'$ describing the direction of the ray 68 before and after refraction by the objective lens 48 (which are very simple to derive based on the system's geometry), the Möller and Hughes method generates a 3×3 matrix describing the transformation which can then be applied to $\hat{e}_s$ and $\hat{e}_p$. The method uses no trigonometric functions or square roots and is up to a factor of four faster than other similar methods. In the present embodiment, a further generalisation is applied so that the inverse matrices (i.e. the matrices that would map $\hat{e}'$ onto $\hat{e}$) are efficiently calculated at the same time.

In order to perform a calculation of the intensity pattern at the detector 58, given a particular sample 50 misalignment described by $\hat{n}$ and a particular model for 's' and 'p' reflectance as a function of angle-of-incidence (derived in a conventional way such as by using standard Fresnel equations or by a more sophisticated technique such as that described in the Applicant's earlier patent application WO2008/119984 for determining the thickness or curvature of a thin film coating or stack of thin film coatings upon the sample 50—referred to in either case as the filmstack model) we proceed as follows for rays 68 associated with each discrete pixel 66 at the detector 58:

1) Using information stored from the system calibration (as will be described below), trace the ray 68 backwards from the detector 58 to the focal point of the objective lens 48, in particular finding the vector $\hat{r}$ which describes the direction of the light ray 68 at that point.
2) Combining $\hat{r}$ with the vector $\hat{n}$ that describes the sample 50 orientation, find the plane of incidence and hence the vectors $\hat{e}_s$ and $\hat{e}_p$ which are perpendicular to $\hat{r}$ and respectively perpendicular and parallel to the plane of incidence.
3) Reflect all three vectors about the normal $\hat{n}$ to obtain the corresponding vectors which describe the ray 68 as it travels from the source 42 side of the objective lens 48 down to the focal point.
4) Apply the inverse Möller and Hughes matrix to each of the three vectors at the objective lens 48 to obtain the vectors describing the ray 68 above the objective lens 48 as it arrives from the source beam 44.
5) Follow the ray 68 back to its source point, (x, y), within the beam 44.
6) Having used the 'time reversal' principle to calculate the geometry of the beam 44 from the detector 58 back to the source 42, we now trace it back in the forwards direction to calculate its intensity. This is performed by using calibration data regarding the intensity of the beam 44 at (x, y), along with its polarisation, to calculate the amplitudes of the electric field components along its initial $\hat{e}_s$ and $\hat{e}_p$ directions.
7) Use the filmstack model to calculate the reflectance as a function of angle-of-incidence and polarisation (i.e. s or p) and find the electric field components along the $\hat{e}_s$ and $\hat{e}_p$ directions after reflection from the sample 50. The reflectance coefficients, and therefore the field amplitude components, will in general be complex numbers because of the phase changes which take place on reflection.
8) At the retarder 52, resolve the field components along $\hat{e}_s$ and $\hat{e}_p$ to find the corresponding components along $\hat{e}_{fast}$ and $\hat{e}_{slow}$, using calibration data for the orientation of the retarder fast axis 60.
9) At the polarizer 54, resolve the field components along the polarisation axis 62 to obtain the field strength along $\hat{e}_{tot}$. This encodes both amplitude and phase information as the two complex components along $\hat{e}_{fast}$ and $\hat{e}_{slow}$ (which derive in turn from the components along $\hat{e}_s$ and $\hat{e}_p$) are forced to interfere with one another as they pass through the polarizer 54.
10) Finally, the intensity at the detector pixel 66 is found by taking the square of the amplitude along $\hat{e}_{tot}$.

It is possible to repeat the above method for a plurality of pixels 66 so as to calculate a full interference pattern at the detector 58 based on a nominal set of parameters that describe the filmstack of the sample 50 and its orientation. In other words, this embodiment of the invention provides a way of generating a predicted interference pattern at the detector 58 given a particular set of parameters describing (a) the coating(s) present on the sample 50 and (b) the sample 50 orientation. Accordingly, with this method, a particular orientation of the sample 50 must be assumed in order to carry out the ray-tracing described.

In order to use the technique to perform a measurement on a sample 50 with unknown properties, it is necessary to perform a nonlinear regression analysis (e.g. using a Levenberg-Marquardt algorithm or similar), in which the set of parameters that describe both the filmstack and the orientation are iteratively improved until the best possible match is obtained between the interference pattern calculated by the method described and a given set of actual measured data.

It will be understood that in the method described above some implicit assumptions are made in order to simplify the procedure. The most significant assumption is that the reflection of a light ray 68 from a sample 50 bearing a coating (i.e. filmstack), is adequately described by a single reflected ray 68 having a modified amplitude and phase. This is not strictly true because of the multiple reflections which take place at each interface within the sample 50, leading to multiple reflected rays 68 with small lateral displacements from one another. However, so long as the sample 50 surface is flat and the apparatus 40 is aligned so that the relay lens 56 casts a focused image of the objective lens's 48 Fourier plane upon the detector 58, this assumption is valid. If, however, the surface of the sample 50 is significantly curved, this assumption becomes invalid for the reasons described in the Applicant's earlier patent application WO2008/119984, and so the present method will need to be revised in order to incorporate the method of WO2008/119984.

Another implicit assumption in the above method is that the intensity of the source 42 varies sufficiently slowly, relative to the density of pixels 66 at the detector 58, that if the pixel 66 pattern of the detector 58 were to be projected onto the source 42 then the intensities of immediately adjacent pixels 66 would be similar. This will certainly hold true if the source is, for example, a Gaussian laser beam, even if contaminated with typical amounts of speckle noise. The effect of this is that when the 'time-reversed' ray 68 is traced back through the objective lens 48 using the inverse Möller and Hughes matrix, the matrices are only available at discrete points and so the traced ray 68 is displaced slightly to the nearest such point. In practice, this effect has been found not to introduce significant errors to the calculated response of the detector 58. In any case, as the calculation of the Möller and Hughes matrices is a one-off event performed during calibration of the system 40, the density of such discrete points can in fact be made arbitrarily high (much higher than the density of detector pixels 66 if need be) without any detriment to the efficiency of the calculation at run-time.

The procedure for calibrating the present system 40 involves determining a set of calibration parameters through use of nonlinear regression on a set of interference patterns obtained from samples with a known filmstack (e.g. $SiO_2$ on Si) but differing thicknesses, preferably where at least one of the thicknesses (preferably for a sample with a thickness close to the laser wavelength) is known independently. The calibration procedure consists of regressing upon the thicknesses and orientations of all the samples simultaneously, together with all the calibration parameters, until the set of calibration parameters is obtained that gives the best fits to the raw data over all the samples while at the same time providing thickness solutions compatible with the known values. The calibration procedure is somewhat simplified if it can be guaranteed that all the calibration samples have the same orientation when they are measured (for example, by using small coupons of silicon carefully mounted on a precision-machined metal block), although this is not essential.

More specifically, the following calibration parameters may be obtained using the calibration procedure described above:

1) The direction of the incident laser beam 44 relative to the main axis of the objective lens 48 (ideally the beam 44 should be perfectly parallel to this axis, once it has reflected off the beamsplitter 46, but deviations from this situation can easily be accommodated within this method).
2) The intensity variation of the incident beam 44 across its profile. This can either be represented by a model, e.g. for a classic Gaussian beam profile, or by a lookup table derived from experimental data gathered for the intensities measured from a sample with known reflectance and orientation.
3) The precise wavelength of the laser.
4) The radial angles of the incident beam 44 polarisation, the retarder 52 orientation, and polarizer 54 orientation, together with the actual retardation of the retarder 52 at the laser wavelength and any degree of ellipticity that may exist within the incident beam 44 polarisation.

It will be understood that embodiments of the present invention provide an apparatus and method which eliminates the need for sample alignment in order to perform an optical measurement technique such as BPR or BPE. In addition, allowances can be made for factors such as misalignment of the incoming laser beam 44 relative to the objective lens 48 axis.

The result of the above method is a calculated intensity value at each pixel 66 of the detector 58 for which the procedure is carried out. The procedure can be carried out at every pixel 66 in the two-dimensional detector array 64, in which case a calculated image of the complete interference fringe pattern will be obtained, or it could be carried out for only a subset of pixels 66—for example, to produce horizontal and vertical profiles through the centre of the interference fringe pattern. In either case, the calculated intensities can be directly compared with the measured intensities found by directly measuring the reflectance from the sample 50.

FIG. 3A shows one such measured fringe pattern 70, taken using the apparatus 40 shown in FIG. 2 where the sample 50 is constituted by a reasonably well-aligned cardiac stent. Thus, it can be seen that the fringe pattern 70 comprises a series of reasonably centred concentric circles. For comparison, FIG. 3B shows a corresponding calculated fringe pattern 72 where the stent was assumed to be perfectly aligned with the apparatus 40.

FIG. 4A shows another measured fringe pattern 74, again, taken using the apparatus 40 shown in FIG. 2 in which the sample 50 is constituted by the stent used to produce the images in FIGS. 3A and 3B, but wherein the stent is misaligned within the apparatus 40. Accordingly, it can be seen that the fringe pattern 74 comprises a series of concentric rings that are centred to the left of the image and which have a greater intensity (brightness) towards the left of the image. For comparison, FIG. 4B shows a corresponding calculated fringe pattern 76 where misalignment of the stent was included in the calculation and, as a result, the image is similarly off-set to the left when compared to the measured result.

It can be seen from the above Figures, that the method and apparatus of the present embodiment enable an intensity pattern to be calculated, which corresponds to the measured results even when the sample is misaligned. Accordingly, optical measurements can be obtained without the need to accurately align the sample in the system. It will also be understood that the nature (or extent) of the misalignment could be obtained from the present method by extracting the parameters relating to the misalignment from the data that has been arrived at to provide the best fit between the calculated image and the measured image.

If it is more convenient to work with reflectance profiles rather than intensity profiles, then if the source 42 intensity pattern and sample 50 orientation are specified it is possible to use the exact same ray-tracing technique described above but to set the reflectance of the sample 50 to 100%, rather than whatever value would be predicted by the model of the filmstack present upon it. If the measured intensity pattern is then divided by the calculated "100% reflectance" intensity pattern, then a 'reflectance map' will be obtained where the value found at each detector pixel 66 corresponds to the reflectance coefficient of the sample 50 surface for light that arrives at that pixel 66.

Figure 5:
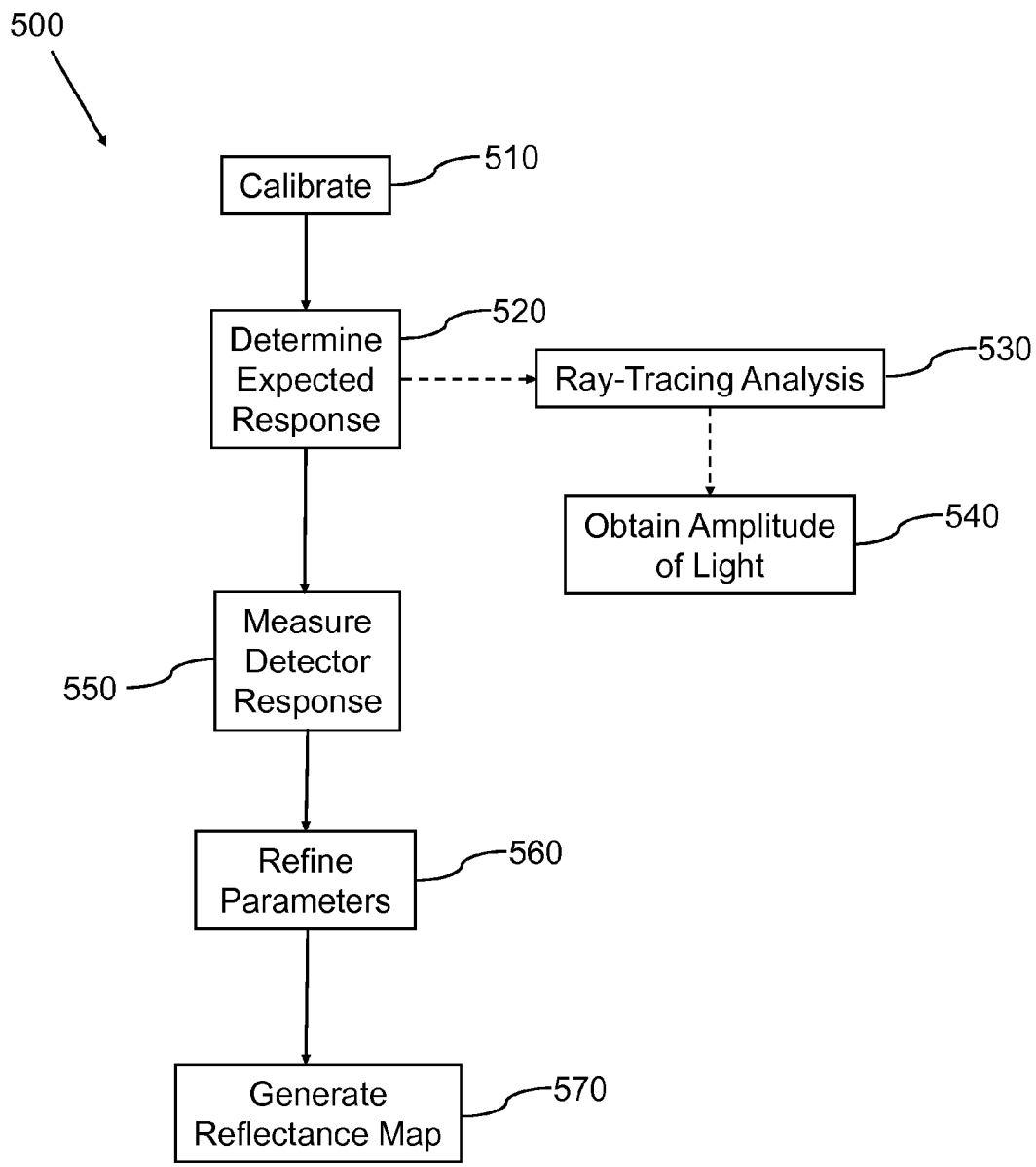
FIG. 5 illustrates a flow chart of a method in accordance with an embodiment of the present invention.

FIG. 5 shows a flow chart of a method 500 in accordance with an embodiment of the present invention as described herein. In an optional step 510, a calibration step is performed. The calibration step may include, for example, determining the intensity characteristics of the light source and/or the alignment of optical elements within the optical measurement apparatus. In step 520, the expected response from the detector in the optical measurement apparatus is determined, given a particular set of parameters defining a path that light can take through the optical measurement apparatus from the light source, via the sample, to the detector. As shown, determining the expected response may include a step 530 of a ray-tracing analysis. The ray-tracing analysis may include the determination of the path of a light ray emerging from the light source and being reflected form the sample to the detector. For example, a light path may be ray-traced from the detector, at the location of a given detector element, and the ray may be followed backwards through the optical measurement apparatus to a point in its source. In various embodiments, a step 540 of obtaining the amplitude of light from the source at the point is performed. In step 550, the response from the detector for the sample under test is measured, and in step 560, the set of parameters is refined until the expected response and the measured response converge so as to determine the set of parameters giving rise to the measured response. In optional step 570, a reflectance map may be generated, where the value obtained at each given detector element corresponds to the reflectance coefficient of the sample for light that arrives at each given detector element.

Figure 6:
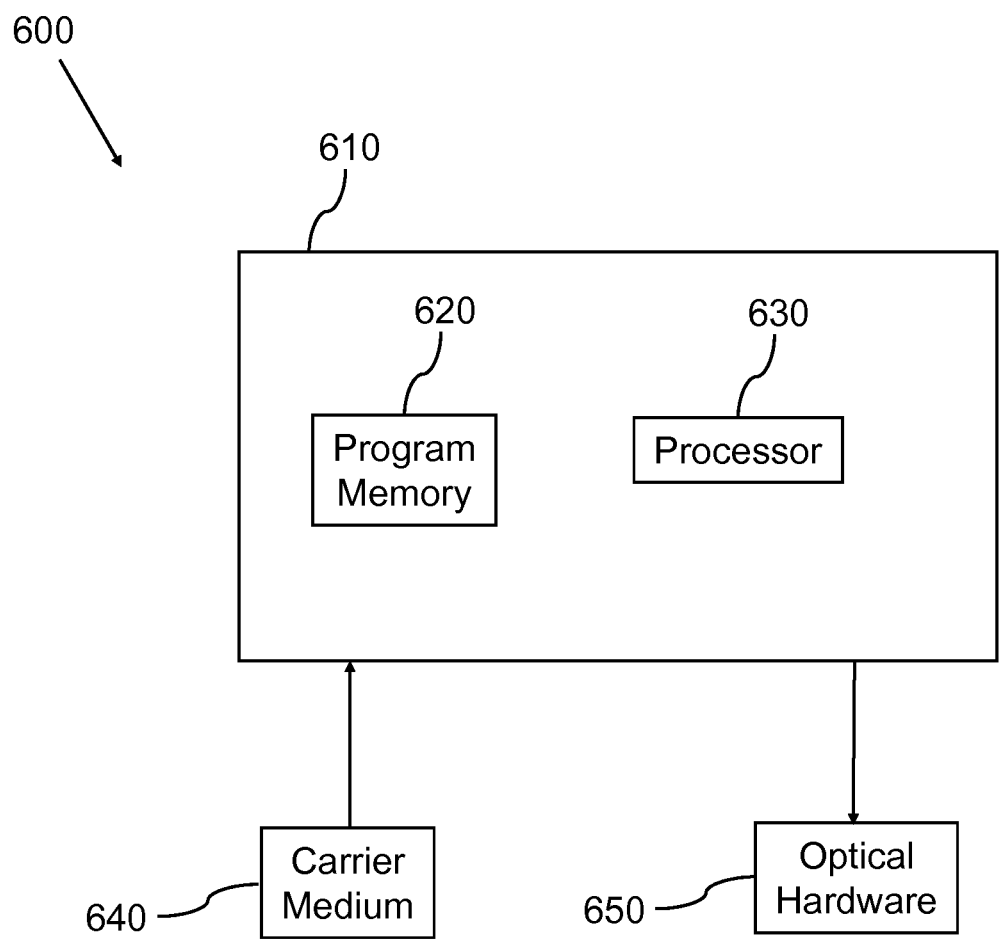
FIG. 6 illustrates schematically an apparatus according to embodiments of the present invention.

FIG. 6 shows a schematic of portions of an apparatus 600 for compensating for sample misalignment in accordance with embodiments of the present invention. As shown, apparatus 600 includes a computer or controller 610 that features a program memory 620 and a processor 630. The computer 610 receives and/or reads various carrier media 640 carrying computer readable program code configured to cause the apparatus 600 to carry out techniques of compensating for sample misalignment detailed herein. The computer 610 also interfaces with various optical hardware 650 and other components, as detailed herein. The computer readable instructions may be stored in the program memory 620 and executed by the processor 630.

It will be appreciated by persons skilled in the art that various modifications may be made to the above embodiments without departing from the scope of the present invention. For example, whilst the above discussion has been primarily concerned with the optical measurement techniques of BPR and BPE, the invention is equally applicable to other optical measurement techniques.

The invention claimed is:

1. A method of compensating for sample misalignment in an optical measurement apparatus, comprising the steps of:
   determining an expected response from a detector in said optical measurement apparatus given a particular set of parameters defining a path that light can take through the optical measurement apparatus from a source, via a sample, to the detector;
   measuring a response from the detector for the sample under test; and
   refining the set of parameters until the expected response and the measured response converge so as to determine the set of parameters giving rise to the measured response,
   wherein the step of determining the expected response from the detector comprises ray-tracing analysis, and wherein the ray-tracing analysis comprises determining the path of a light ray emerging from a light source and being reflected from the sample to the detector.

2. The method according to claim 1 wherein the step of determining the expected response comprises the calculation of a reflected intensity.

3. The method according claim 1 wherein the step of determining the expected response comprises the calculation of a reflectance.

4. The method according to claim 1 wherein the ray-tracing analysis is performed from the detector to the light source and further comprises determining the path of the light ray through one or more optical elements.

5. The method according to claim 1 wherein the ray-tracing analysis is performed from the detector to the light source.

6. The method according to claim 5 wherein the ray-tracing analysis comprises ray-tracing a light path starting from the detector, at the location of a given detector element, and following the ray backwards through the optical measurement apparatus to a point in its source.

7. The method according to claim 6 wherein the step of determining the expected response from the detector further comprises obtaining the amplitude of light from the source at said point.

8. The method according to claim 7 comprising using the amplitude and at least one of (a) the transmission characteristics of the light path or (b) the reflection characteristics of the light path to determine the intensity of the light when it reaches the detector element.

9. The method according to claim 8 wherein the steps of ray-tracing the light path, obtaining the amplitude of light from the source and determining the intensity of the light at the detector element are repeated for one or more alternative light paths that the light may travel through the apparatus or sample to arrive at the given detector element.

10. The method according to claim 9 further comprising the step of combining the intensities of each light ray at the detector element to obtain the total intensity expected.

11. The method according to claim 10 further comprising repeating the steps of claim 16 for a plurality of given detector elements.

12. The method according to claim 11 comprising the step of generating a reflectance map wherein the value obtained at each given detector element corresponds to the reflectance coefficient of the sample for light that arrives at each given detector element.

13. The method according to claim 11 wherein the reflectance map is obtained by performing the ray-tracing analysis for a sample of known orientation and setting the reflectance of the sample to 100%, and then dividing the measured intensity pattern by the calculated 100% reflectance.

14. The method according to claim 1 wherein the step of refining the set of parameters comprises one of (a) regression analysis, (b) non-linear regression analysis, or (c) use of a Levenberg-Marquardt algorithm.

15. The method according to claim 1 further comprising a calibration step comprising determining at least one of (a) the intensity characteristics of the light source or (b) the alignment of optical elements within the optical measurement apparatus.

16. The method according to claim 1 configured for compensating for sample misalignment during any one of Beam Profile Reflectometry (BPR), Beam Profile Ellipsometry (BPE), Spectrophotometry, Spectroscopic Ellipsometry, or an alternative optical measurement technique.

17. An optical measurement apparatus for compensating for sample misalignment, comprising:
   a detector for measuring a response from a sample under test; and
   a processor for determining an expected response from the detector given a particular set of parameters defining a path that light can take through the optical measurement apparatus from a source, via a sample, to the detector and for refining the set of parameters until the expected response and the measured response converge so as to determine the set of parameters giving rise to the measured response,
   wherein determining the expected response from the detector comprises ray-tracing analysis, and wherein the ray-tracing analysis comprises determining the path of a light ray emerging from a light source and being reflected from the sample to the detector.

18. A non-transitory carrier medium carrying computer readable program code configured to cause a computer to carry out the method according to claim 1.

19. A device comprising:
a program memory containing computer readable instructions; and
a processor configured to read and execute instructions stored in said program memory;
wherein said processor readable instructions comprise instructions configured to control said device to carry out the method according to claim 1.

\* \* \* \* \*